US011802315B2

(12) United States Patent
Ruijtenbeek et al.

(10) Patent No.: US 11,802,315 B2
(45) Date of Patent: Oct. 31, 2023

(54) METHOD FOR PREDICTING THE RESPONSE OF NON-SMALL-CELL LUNG CARCINOMA PATIENTS TO A MEDICAMENT

(71) Applicants: PamGene B.V., 's-Hertogenbosch (NL); Erasmus University Medical Center Rotterdam, Rottterdam (NL)

(72) Inventors: Robby Ruijtenbeek, Utrecht (NL); Dirgje Maria Adriana Van Den Heuvel, Opijnen (NL); Richard De Wijn, Nijmegen (NL); Joan Gertrudis Jacobus Victor Aerts, Rotterdam (NL); Adrianus Henricus Josephus Mathijssen, Barendrecht (NL)

(73) Assignees: PamGene B.V., 's-Hertogenbosch (NL); Erasmus University Medical Center Rotterdam, Rotterdam (NL)

( * ) Notice: Subject to any disclaimer, the term of this patent is extended or adjusted under 35 U.S.C. 154(b) by 620 days.

(21) Appl. No.: 16/633,389

(22) PCT Filed: Aug. 9, 2018

(86) PCT No.: PCT/EP2018/071569
§ 371 (c)(1),
(2) Date: Jan. 23, 2020

(87) PCT Pub. No.: WO2019/030311
PCT Pub. Date: Feb. 14, 2019

(65) Prior Publication Data
US 2020/0232043 A1     Jul. 23, 2020

(30) Foreign Application Priority Data

Aug. 9, 2017 (EP) .................................... 17185467

(51) Int. Cl.
*C12Q 1/6886* (2018.01)
*C12Q 1/48* (2006.01)

(52) U.S. Cl.
CPC ........... *C12Q 1/6886* (2013.01); *C12Q 1/485* (2013.01); *G01N 2440/14* (2013.01); *G01N 2800/52* (2013.01); *G01N 2800/7028* (2013.01)

(58) Field of Classification Search
None
See application file for complete search history.

(56) References Cited

U.S. PATENT DOCUMENTS

| 8,962,267 B1* | 2/2015 | De Wijn ................ C12Q 1/485 506/10 |
| 2010/0234238 A1 | 9/2010 | Versele et al. |
| 2013/0217055 A1 | 8/2013 | Boender et al. |
| 2019/0112633 A1* | 4/2019 | Ruijtenbeek ....... G01N 33/5743 |

FOREIGN PATENT DOCUMENTS

| EP | 1983002 A2 | 10/2008 | |
| WO | 2008049930 A2 | 5/2008 | |
| WO | WO-2008049930 A2 * | 5/2008 | ............ C12Q 1/485 |
| WO | 2010116003 A2 | 10/2010 | |
| WO | WO-2012049329 A1 * | 4/2012 | ............ C12Q 1/485 |

OTHER PUBLICATIONS

Karlsson (Evaluation of Intracellular Signaling Downstream Chimeric Antigen Receptors, PLOS One, 2015): (Year: 2015).*
Noe et al. (Clinical and kinomic analysis identifies peripheral blood mononuclear cells as a potential pharmacodynamic biomarker in metastatic renal cell carcinoma patients treated with sunitinib, Oncotarget, vol. 7, 2016) (Year: 2016).*
Bellesoeur et al. (Abstract 2038: Sunitinib impact on kinome profiles of peripheral blood mononuclear cells from renal cell carcinoma patients: Do molecular effects correlate with clinical data, Cancer Research, 2016). (Year: 2016).*
Gridelli (2017) (Predictive biomarkers of immunotherapy for non-small cell lung cancer: results from an Experts Panel Meeting of the Italian Association of Thoracic Oncology, Review Article, 2017) (Year: 2017).*
International Search Report and Written Opinion dated Nov. 15, 2018 for PCT International Patent Application No. PCT/EP2018/071569.
PCT Demand for International Preliminary Examination (Chapter II) dated May 28, 2019 for PCT International Patent Application No. PCT/EP2018/071569.
Second Written Opinion dated Jul. 3, 2019 for PCT International Patent Application No. PCT/EP2018/071569.
Response to Jul. 3, 2019 Written Opinion dated Aug. 22, 2019 for PCT International Patent Application No. PCT/EP2018/071569.

(Continued)

*Primary Examiner* — Laura B Goddard
*Assistant Examiner* — Sarah A Alsomairy
(74) *Attorney, Agent, or Firm* — Amster, Rothstein & Ebenstein LLP

(57) ABSTRACT

The present invention relates to a method for determining or predicting the response of a patient diagnosed with non-small-cell lung carcinoma to targeted pharmacotherapy. The present invention also aims to provide methods and devices for predicting the response of patients diagnosed with non-small-cell lung carcinoma to specific medicaments. More specifically, the present invention provides methods which measure kinase-activity by studying phosphorylation levels and profiles and inhibitions thereof by drugs in blood samples of said patients.

8 Claims, 6 Drawing Sheets
Specification includes a Sequence Listing.

(56) References Cited

OTHER PUBLICATIONS

Notification Concerning Informal Communications with the Applicant dated Sep. 18, 2019 for PCT International Patent Application No. PCT/EP2018/071569.

International Preliminary Report on Patentability dated Oct. 30, 2019 for PCT International Patent Application No. PCT/EP2018/071569.

China National Intellectual Property Administration, "The First Office Action", issued in Chinese Patent Application No. 201880051867.6, which is a counterpart to U.S. Appl. No. 16/633,389, dated Feb. 3, 2023, 21 pp. (14 pages of English Translation of Office Action and 7 pages of original Office Action).

* cited by examiner

METHOD FOR PREDICTING THE RESPONSE OF NON-SMALL-CELL LUNG CARCINOMA PATIENTS TO A MEDICAMENT

CROSS-REFERENCE TO RELATED APPLICATIONS

This application is a U.S. national stage entry under 35 U.S.C. § 371 of PCT International Patent Application No. PCT/EP2018/071569, filed Aug. 9, 2018, which claims priority to European Patent Application No. 17185467.2, filed Aug. 9, 2017, the contents of which are incorporated herein by reference in their entirety.

FIELD OF THE INVENTION

The present invention relates to methods and devices for determining or predicting the response of a patient diagnosed with non-small cell lung carcinoma to specific medicaments. More specifically, the present invention provides methods which measure kinase activity by studying phosphorylation levels and profiles in samples, preferably blood samples, of said patients.

BACKGROUND OF THE INVENTION

At present lung cancer is considered to be one of the most important causes of death, especially in adults at the ages from 50 to 69 years old. Long term exposure to smoking is the cause of lung cancer for 90% of the cases. Among male smokers, the lifetime risk of developing lung cancer is about 17%; among female smokers the risk is about 11%. For non-smokers, the risk of developing lung cancer is about 1%. The main causes for lung cancer in non-smokers are genetic factors, radon gas, asbestos, air pollution and passive smoking. There are two main types of lung cancer: non-small cell lung cancer (NSCLC) (in about 80% of the cases) and small cell lung cancer (in about 17% of the cases). NSCLC can further be classified according to the growth type and spread of the cancer cells. NSCLC can therefore be classified into squamous cell carcinoma, large cell carcinoma and adenocarcinoma. Adenocarcinoma is more frequent in women, Asians and non-smokers. Other less common types of NSCLC are pleomorphic, carcinoid tumor, salivary gland carcinoma, and unclassified carcinoma.

For the diagnosis of NSCLC a lung tissue biopsy is taken. Based on a primary biopsy diagnosis nearby lymph nodes may be biopsied to see if the cancer has spread. Staging of NSCLC is based on the American Joint Committee on Cancer (AJCC) TNM system.

The T stands for tumor (how far it has grown within the lung and other factors). The T category is assigned a number (from 0 to 4) based on the tumor's size. N stands for spread to nearby lymph nodes (bean-sized collections of immune system cells, to which cancers often spread first). The N category is assigned a number (from 0 to 3) based on whether the NSCLC cells have spread to lymph nodes or are found in the lymphatic channels connecting the lymph nodes. The M category is based on whether the NSCLC has metastasized (spread) to distant organs, which organs it has reached. It is generally known that most types of lung cancer have a poor prognosis. According to the TNM standards the different stages and survival in the United States are as follows:

Stage IA: The 5-year survival rate is around 49%.
Stage IB: The 5-year survival rate is around 45%.
Stage IIA: The 5-year survival rate is around 30%.
Stage IIB: The 5-year survival rate is around 30%.
Stage IIIA: The 5-year survival rate is around 14%.
Stage IIIB: The 5-year survival rate is around 5%.
Stage IV: The 5-year survival rate is about 1%-2%.

NSCLC treatment options are based on the stage of the disease and may include: surgery, chemotherapy, targeted therapy, immunotherapy and radiation therapy. Early-stage NSCLC can often be cured with surgery alone, but more advanced NSCLC can be much harder to treat because standard cancer treatments such as chemotherapy are not very effective. But in recent years, newer types of immunotherapy and targeted therapies have changed the treatment of this disease, and many new treatments have shown a great deal of promise in treating advanced NSCLC.

The development of molecularly targeted therapy (e.g. small molecules and monoclonal antibodies) has significantly improved outcomes in the metastatic setting for patients with NSCLC whose tumors harbor activated oncogenes such as epidermal growth factor receptor (EGFR) and translocated genes like anaplastic lymphoma kinase (ALK). In addition, immune checkpoint inhibitors have been successfully used to treat NSCLC.

This therapy is based upon the fact that T lymphocytes are critical to antitumor immunity, and this antitumor immunity requires activation by an antigen-specific T cell receptor in the context of costimulatory activation. Excess immune activation is being prevented by a naturally occurring feedback mechanism that leads to the expression of negative costimulatory molecules ("checkpoints"). Examples of such checkpoints are cytotoxic T-lymphocyte antigen 4 (CTLA-4), programmed death 1 (PD-1), T cell immunoglobulin 3, and lymphocyte-activation gene 3. Antibodies directed against these checkpoints may restore or augment an antitumor immune response and produce tumor responses in patients with advanced or metastatic NSCLC. Examples of such antibodies are Nivolumab (PD-1 inhibition), Atezolizumab (PD-L1 inhibition), Avelumab (PD-L1 inhibition) and Pembrolizumab (PD-1 inhibition).

In particular, stage IV NSCLC is very hard to cure, as they have already spread to distant lymph nodes or other areas of the body. While the lung tumors can often be removed by surgery or treated with radiation therapy, metastases in internal organs which cannot be removed may be treated with radiation, immunotherapy, targeted therapy, or chemotherapy. Checkpoint inhibitors can be used alone or in combination. Though, not all patients respond to these therapies. Approximately 30-50% of the patients treated with a checkpoint inhibitor respond to this drug. For combinatorial treatment with checkpoint blockers, typically more than 50% of the patients show a positive response.

Unfortunately, most anti-tumor treatments are associated with undesirable side effects, such as profound nausea, vomiting, or severe fatigue. Also, while anti-tumor treatments have been successful, they do not produce significant clinical responses in all patients who receive them resulting in undesirable side effects, delays, and costs associated with ineffective treatment. Therefore, biomarkers that can be used to predict the response of a subject to an antitumor agent prior to administration thereof are greatly needed.

Given the high incidence of NSCLC and limited efficacy of current treatments, an immuno-oncology therapy prediction NSCLC biomarker and assay for an immuno-oncology therapy prediction NSCLC biomarker is needed.

Also, assays for NSCLC biomarkers as an accurate early indicator for therapeutic response typically require taking a lung tissue biopsy which is considered very unpleasant for the patient.

In view of the above, there remains a pressing need for improved methods that provide a fast and accurate prediction of the response of a patient diagnosed with NSCLC to targeted pharmacotherapy, and immuno-oncology in particular.

SUMMARY OF THE INVENTION

Drug response between individuals differs. Drugs can work more or less efficient; but can also induce adverse drug reactions, toxicity and side effects.

The present invention provides methods and devices that enable the determination of the response of a patient diagnosed with NSCLC to targeted pharmacotherapy by measuring kinase activity of a sample from said patient.

The present invention further provides a method for predicting the response of a patient diagnosed with non-small-cell lung carcinoma, to a medicament, comprising the steps of:

(a) measuring the kinase activity of a blood sample, obtained from said patient diagnosed with non-small-cell lung carcinoma, by contacting said sample with at least one protein kinase substrate, thereby providing a phosphorylation profile of said sample, said phosphorylation profile comprising the phosphorylation levels of phosphorylation sites present in at least 5, preferably at least 8 or at least 12, peptide markers as listed in Table 1; and, (b) determining from said phosphorylation profile the response of said patient to said medicament.

In particular embodiments, said blood sample comprises peripheral blood mononuclear cells.

In particular embodiments, said medicament is chosen from the group consisting of Nivolumab, Prembrolizumab, BMS-936559, Atezolizumab, Ipilimumab, Pidilizumab, Avelumab and Durvalumab.

In particular embodiments, said phosphorylation profiles comprise the phosphorylation levels of phosphorylation sites present in at least 10 of the peptide markers as listed in Table 1.

In particular embodiments, said phosphorylation profiles comprise the phosphorylation levels of phosphorylation sites present in the peptide markers as listed in Table 1.

In particular embodiments, step (b) is replaced by a step (c) calculating a classifier parameter from said phosphorylation profile; and a step (d) determining the response of said patient to said medicament on the basis of said classifier parameter.

In particular embodiments, said classifier parameter indicates said patient being a good responder to said medicament if said classifier parameter is above a first predetermined threshold level, and wherein said classifier parameter indicates said patient being a poor responder to said medicament if said classifier parameter is below a second predetermined threshold level.

In particular embodiments, step (b) is replaced by a step (e) comparing said phosphorylation profile to a first and a second reference phosphorylation profile; said first reference phosphorylation profile being representative for a good responder to said medicament and said second reference phosphorylation profile being representative for a poor responder to said medicament; and a step (f) determining response of said patient to said medicament on the basis of the comparison of said phosphorylation profile with said first and said second reference phosphorylation profile.

In particular embodiments, said phosphorylation profile or said classifier parameter indicates good response, poor response or undetermined response of said patient to said medicament.

In particular embodiments, said non-small-cell lung carcinoma is a stage IV non-small-cell lung carcinoma.

In particular embodiments, the toxicity of said medicament in said patient is determined from the measurements in step (a).

Another aspect provides the use of the method as described above for accessing susceptibility to a medicament of a patient having non-small-cell lung carcinoma.

Another aspect provides the use of the method as described above for assessing the pharmaceutical or clinical value of a medicament.

Another aspect provides a kit for determining the response of a patient diagnosed with non-small-cell lung carcinoma to a medicament, comprising at least one array comprising at least 5 peptide markers as listed in Table 1, and a computer readable storage medium having recorded thereon one or more programs for carrying out the method as described above.

Another aspect provides a computer program product for use in conjunction with a computer having a processor and a memory connected to the processor, said computer program product comprising a computer readable storage medium having a computer program mechanism encoded thereon, wherein said computer program mechanism is loaded into the memory of said computer and causes said computer to carry out the method as described above. These and further aspects and embodiments are described in the following sections and in the claims.

4 and 14), zeta chain of T-cell receptor associated protein kinase 70 (ZAP70; SEQ ID NO 5): mitogen-activated protein kinase 1 (MK01; SEQ ID NO 6), protein tyrosine kinase 2 beta (FAK2; SEQ ID NO: 7), Paxillin (PAXI; SEQ ID NO: 8) and 3-phosphoinositide-dependent protein kinase 1 (PDPK1; SEQ ID NO: 21)

Figure 3:
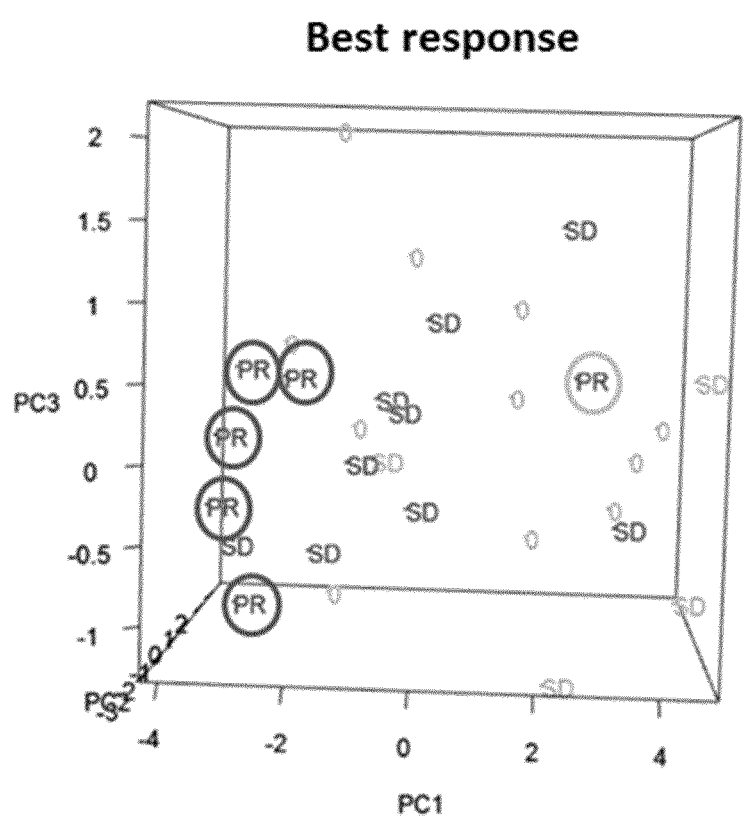

FIG. 3 shows that the kinase activity profiling of non-small cell lung cancer (NSCLC) patient-derived peripheral blood mononuclear cell (PBMC) samples of Nivolumab-treated patients with partial response (PR) cluster together in a principal component analysis (PCA) (5 out of 6). Hence, the method according to the invention allows a good prediction of the treatment outcome of patients treated with Nivolumab.

Figure 4:
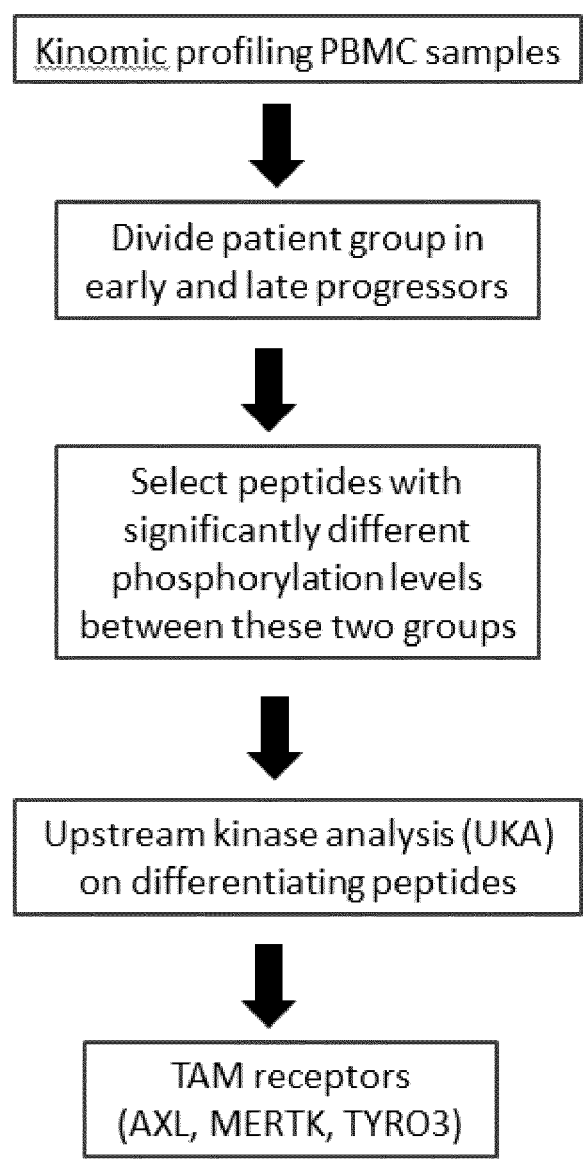

FIG. 4 shows the workflow of an upstream kinase analysis on peptide sequences found to be differentiating between early and late progressive patients. This analysis reported TAM receptor kinases. This family of immunoreceptors comprises the kinases MERTK, TYRO3 and AXL. The 5 most important peptides sequences reporting these aberrant TAM kinase activities are listed in table 1, and include ZAP70 (SEQ ID NO:5), DYR1A (SEQ ID NO: 11), FGFR3 (SEQ ID NO: 13), KSYK (SEQ ID NO: 16) and PRRX2 (SEQ ID NO: 20).

DETAILED DESCRIPTION OF THE INVENTION

Before the present method and devices used in the invention are described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, the preferred methods and materials are now described.

In this specification and the appended claims, the singular forms "a", "an", and "the" include plural references unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The terms "comprising", "comprises" and "comprised of" also include the term "consisting of".

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

The present invention provides methods and devices that enable the determination of the response of a patient diagnosed with NSCLC to targeted pharmacotherapy by measuring kinase activity of a blood sample, obtained from said patient diagnosed with NSCLC. The present invention further shows how the method and devices can be used to predict the response and/or resistance, especially the response, of patients diagnosed with NSCLC to a specific medicament. The method of the present invention therefore adds to the existing assays currently used to select therapies in NSCLC patients.

The method according to the present invention can be used to predict or assess both primary and secondary resistance to a specific medicament. With primary resistance is meant resistance in NSCLC patients that never respond to a specific medicament. In secondary resistance is meant resistance in NSCLC patients which first respond to a specific medicament, but after a few months or years, resistance occurs. For purposes of the present invention, and as used herein the term "kinase activity" or "protein kinase activity" refer to the formation of reaction product(s) by a certain amount of kinase or protein kinase acting on a substrate during the course of the assay.

Protein kinase activity is referred to as the activity of protein kinases. A protein kinase is a generic name for all enzymes that transfer a phosphate to a protein. About two percent of the human genome contains transcription information for the formation of protein kinases. Currently, there are about 518 known different protein kinases. However, because three to four percent of the human genome is a code for the formation of protein kinases, there may be many more separate kinases in the human body.

A protein kinase is a kinase enzyme that modifies other proteins by covalently coupling phosphate groups to them. This process or activity is also referred to as phosphorylation.

Phosphorylation can therefore be regarded as the process of the addition of a phosphate group to a substrate. Phosphorylation usually results in a functional change of the substrate by changing kinase activity, cellular location, or association with other proteins. Up to 30 percent of all proteins may be modified by kinase activity, and kinases are known to regulate the majority of cellular pathways, especially those involved in signal transduction, the transmission of signals within the cell. The chemical activity of a kinase involves removing a phosphate group from ATP or GTP and covalently attaching it to amino acids such as serine, threonine, tyrosine, histidine, aspartic acid and/or glutamic acid that have a free hydroxyl group. Most known kinases act on both serine and threonine, others act on tyrosine, and a number act on all serine, threonine and tyrosine.

The protein kinase activity monitored with the method of the present invention is preferably directed to protein kinases acting towards serine, threonine and/or tyrosine, preferably acting on both serine and threonine, on tyrosine or on serine, threonine and tyrosine and more preferably the method of the present invention if preferably directed to protein kinases acting towards tyrosine.

Protein kinases are distinguished by their ability to phosphorylate substrates on discrete sequences. These sequences have been determined by sequencing the amino acids around the phosphorylation sites and are usually distinct for each protein kinase. The recognition sequence on each substrate is specific for each kinase catalyst.

Because protein kinases have profound effects on a cell, their activity is highly regulated. Kinases are turned on or off by for instance phosphorylation, by binding of activator proteins or inhibitor proteins, or small molecules, or by controlling their location in the cell relative to their substrates. Deregulated activity is a frequent cause of disease, particularly cancer, where kinases regulate many aspects that control cell growth, movement and death. Therefore monitoring the protein kinase activity in tissues can be of great importance and a large amount of information can be obtained when comparing the kinase activity of different tissue samples.

As described in the present invention, the inventors have surprisingly found that the response of a patient diagnosed with NSCLC to targeted pharmacotherapy can be predicted and/or determined on the basis of the measurement of the kinase activity, preferably protein kinase activity, of a sample taken from said patient diagnosed with NSCLC. The methods according to present invention enable to provide information regarding the efficacy of the targeted pharmacotherapy treatment, and more specifically provide an early determination of the most suited treatment of the NSCLC patient.

The measurement of the kinase activity is performed by contacting a sample from a patient diagnosed NSCLC with one or more kinase substrates, preferably protein kinase substrates, thereby generating one or more phosphorylation profile(s).

Said protein kinase substrates as used herein, are preferably peptides, proteins or peptide mimetics. The protein kinase substrates each comprise, preferably one or more, phosphorylation sites that can be phosphorylated by the protein kinases present in the sample. Therefore, exposure of a protein kinase substrate to a sample comprising a protein kinase results in the phosphorylation of one or more of the phosphorylation sites of the protein kinase substrate. This phosphorylation activity can be measured using techniques known in the art. Therefore, during the measurement method the kinase enzymes present in the sample will phosphorylate, preferably one or more, of the phosphorylation sites on one or more protein kinase substrate. The inventors have observed essential differences between kinase activity of NSCLC tumors having a different response to targeted pharmacotherapy. Consequently, the inventors have observed that the kinases present in a sample from patients suffering from NSCLC will phosphorylate protein kinase substrates differently depending on the response to targeted pharmacotherapy with which the patient is envisaged to be treated or is being treated. Phosphorylation signals differ between the samples, resulting in phosphorylation patterns that differ depending on response to targeted pharmacotherapy.

For purposes of the present invention, and as used herein the term "pharmacotherapy", or "pharmacotherapeutics" or "drug treatment" refers to the use of a pharmaceutical drug, also referred to as medicine or medicament wherein said pharmacotherapy is intended for use in the diagnosis, cure, mitigation, treatment, or prevention of disease.

The present invention therefore provides in a method for predicting the response of a patient diagnosed with NSCLC, to a medicament, comprising the steps of:
(a) measuring the kinase of a sample, obtained from said patient diagnosed with NSCLC, by contacting said sample with at least one protein kinase substrate, thereby providing a phosphorylation profile of said sample, said phosphorylation profile comprising the phosphorylation levels of phosphorylation sites present in at least 5, preferably at least 8 or at least 12, peptide markers as listed in Table 1; and,
(b) determining from said phosphorylation profile the response of said patient to said medicament.

It is clear that effects of a medicament can be monitored using the method according to the invention as described herein. The medicament affects the degree of inhibition, the potency and/or the selectivity of the kinases in the sample. More peptide inhibition is caused by the larger effect of the medicament on the kinases in the sample and therefore the drug is less selective. Also an increased peptide inhibition would lead to a larger amount of normal tissues being affected by the drug, making the drug less tumor tissue specific.

As referred to in the present application NSCLC regards one of the main types of lung cancer and accounts for about 85% of all lung cancers. NSCLC can be further divided into three subtypes, namely squamous cell carcinoma, large cell carcinoma and adenocarcinoma. Adenocarcinoma is the most common type and starts in the mucus making gland cells in the lining of the airways, squamous cell cancer develops in the flat cells that cover the surface of the airways and grows near the centre of the lung and large cell carcinoma appear large and round under the microscope. Other less common types of NSCLC are pleomorphic, carcinoid tumor, salivary gland carcinoma, and unclassified carcinoma.

As used in the present invention, the term "sample" refers to a sample obtained from an organism (patient) such as human or from components (e.g. tissue or cells) of such an organism. Blood is considered a specialized form of connective tissue. Therefore, the sample can be a blood sample. Lung tissue biopsies are considered unpleasant for the patient. Therefore, other samples than NSCLC tumor tissue samples are preferred.

In the present invention, said sample is preferably obtained from a patient diagnosed with NSCLC and is preferably derived from the blood of said patient. More preferably, said blood sample comprises peripheral blood monocytes (PBMCs).

Said sample is preferably a fresh or a fresh frozen sample.

More preferably, said sample refers to a lysate of blood-derived PBMCs, which are preferably isolated by Ficoll-Isopaque density centrifugation or by any methods known in the art.

In a preferred embodiment of the present invention said sample is a sample that has undergone a preparation step prior to the steps according to the method of the present invention. Preferably said preparation step is a step where the protein kinases present in said sample are released from the tissue by lysis. Additionally the kinases in the sample may be stabilized, maintained, enriched or isolated, and the measurement of the kinase activity as performed in step (a) occurs on the enriched or isolated protein kinase sample. By first enriching protein kinases in the sample or isolating protein kinases from the sample the subsequent measurement of the kinase activity will occur in a more efficient and reliable manner. Also the clarity and intensity of the obtained phosphorylation signal will be increased as certain contaminants are being removed during the enriching or isolating step.

In particular embodiments, said sample is obtained from a patient diagnosed with NSCLC and refractory to a first line therapy (e.g. platinum-based therapy).

In particular embodiments, said sample is obtained from a patient diagnosed with NSCLC before onset of treatment with a second line therapy (e.g. immune checkpoint inhibitors such as Nivolumab, Pembrolizumab, Ipilimumab, Pidilizumab, Avelumab, Durvalumab, BMS-936559, Atezolizumab and/or a combination thereof and/or a combination thereof and/or analogs thereof, preferably Nivolumab).

As used in the present invention, the term "phosphorylation profile" refers to a data set representative for the phosphorylation levels of, preferably one or more, phosphorylation sites present on the protein kinase substrates. When measuring the kinase activity of a sample by contacting said sample with protein kinase substrates a specific phosphorylation profile is obtained. The phosphorylation profile is generated by the phosphorylation of the protein kinase substrates with the protein kinases present in the sample and it comprises the level of phosphorylation of the phosphorylation sites present on the protein kinase substrates used. A phosphorylation profile can thus be generated when using at least one protein kinase substrate in different test conditions such as for example by comparing the phosphorylation of a sample on one peptide or protein (protein kinase substrate) in the presence and absence of a phosphatase modulating compound or medicament. More frequently phosphorylation profiles of a sample will be measured using several protein kinase substrates in the same or sequentially carried out experiments. Preferably, the present invention determines tyrosine, serine and threonine kinase activity levels or profiles.

It should be noted that a person skilled in the art will appreciate that the methods of the present invention can use phosphorylation profiles as a basis for determining and predicting the response to a medicament of a patient suffering from NSCLC. However, the phosphorylation levels of individual protein kinase substrates can also be used as a basis for determining or predicting the resistance to a medicament of a patient suffering from NSCLC.

It should be noted that for the measurement of the protein kinase activity, ATP or any other phosphate source needs to be added to the sample when it is contacted with the protein kinase substrates. The presence of ATP will lead to a phosphorylation of the protein kinase substrates. Alternatively, the phosphorylation of the protein kinase substrates can be performed in the absence of exogenous ATP. When no ATP is added during the incubation of the sample with the protein kinase substrates, the endogenous ATP, the ATP naturally present in the sample, will act as the primary source of ATP.

The phosphorylation level of each of the protein kinase substrates can be monitored using any method known in the art. The response of the protein kinase substrates is determined using a detectable signal, said signal resulting from the interaction of the sample with the protein kinase substrates or by for instance measuring mass differences using mass spectrometry. In determining the interaction of the sample with the protein kinase substrates the signal is the result of the interaction of the phosphorylated substrates with a molecule capable of binding to the phosphorylated substrates. This binding can be detected by e.g. surface plasmon resonance or by the molecule being detectably labelled. For the latter, the molecule that specifically binds to the substrates of interest (e.g. antibody or polynucleotide probe) can be detectably labelled by virtue of containing an atom (e.g. radionuclide), molecule (e.g. fluorescein), or enzyme or particle or complex that, due to a physical or chemical property, indicates the presence of the molecule. A molecule may also be detectably labelled when it is covalently bound to or otherwise associated with a "reporter" molecule (e.g. a biomolecule such as an enzyme) that acts on a substrate to produce a detectable atom, molecule or other complex.

Detectable labels suitable for use in the present invention include any composition detectable by spectroscopic, photochemical, biochemical, immunochemical, electrical, optical or chemical means. Labels useful in the present invention include biotin for staining with labelled avidin or streptavidin conjugate, magnetic beads (e.g. Dynabeads'), fluorescent dyes (e.g. fluorescein, fluorescein-isothiocyanate (FITC), Texas red, rhodamine, green fluorescent protein, enhanced green fluorescent protein and related proteins with other fluorescence emission wavelengths, lissamine, phycoerythrin, Cy2, Cy3, Cy3.5, Cy5, Cy5.5, Cy7, FluorX [Amersham], SYBR Green I & II [Molecular Probes], and the like), radiolabels (e.g. 3H, 125I, 35S, 14C, or 32P), enzymes (e.g. luciferases, hydrolases, particularly phosphatases such as alkaline phosphatase, esterases and glycosidases, or oxidoreductases, particularly peroxidases such as horse radish peroxidase, and the like), substrates, cofactors, chemilluminescent groups, chromogenic agents, and colorimetric labels such as colloidal gold or coloured glass or plastic (e. g. polystyrene, polypropylene, latex, etc.), protein particles or beads. In particular, all detectable labels well known to those skilled in the art may be used as detectable labels for use in the present invention.

Means of detecting such labels are well known to those of skill in the art. Thus, for example, chemiluminescent and radioactive labels may be detected using photographic film or scintillation counters, and fluorescent markers may be detected using a photodetector to detect emitted light (e.g. as in fluorescence-activated cell sorting). Enzymatic labels are typically detected by providing the enzyme with a substrate and detecting a coloured reaction product produced by the action of the enzyme on the substrate. Colorimetric labels are detected by simply visualizing the coloured label. Thus, for example, where the label is a radioactive label, means for detection include a scintillation counter, photographic film as in autoradiography, or storage phosphor imaging. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Also, simple colorimetric labels may be detected by observing the colour associated with the label. Fluorescence resonance energy transfer has been adapted to detect binding of unlabeled ligands, which may be useful on arrays.

In a particular embodiment of the present invention the response of the protein kinase substrates to the sample is determined using detectably labelled antibodies; more in particular fluorescently labelled antibodies. In those embodiments of the invention where the substrates consist of protein kinase substrates, the response of the protein kinase substrates is determined using fluorescently labelled anti-phosphotyrosine antibodies, fluorescently labelled anti-phosphoserine or fluorescently labelled anti-phosphothreonine antibodies. The use of fluorescently labelled anti-phosphotyrosine antibodies or fluorescently labelled anti-phosphoserine or fluorescently labelled anti-phosphothreonine antibodies in the method of the present invention, allows real-time or semi real-time determination of the protein kinase activity and accordingly provides the possibility to express the protein kinase activity as the initial velocity of protein kinase derived from the activity over a certain period of incubation of the sample on the substrates.

Moreover, the measurement of the kinase activity of said sample preferably occurs by contacting said sample with at least 5, preferably at least 8 or at least 12, the peptide markers as listed in Table 1.

In another embodiment according to the present invention, the phosphorylation profiles comprise the phosphorylation levels of phosphorylation sites present in at least 10 or at least 20 of the peptide markers as listed in Table 1. Preferably phosphorylation levels will be studied of phosphorylation sites present in at least 5, 6, 7, 8, 9, 10, 11, 12, 13, 14, 15, 16, 17, 18, 19, 20, 21 or 22 of the peptide markers listed in Table 1. More preferably phosphorylation levels will be studied of phosphorylation sites present in at least 5 or at least 8 or at least 12 of the peptide markers listed in Table 1. In another embodiment according to the present invention, the phosphorylation profiles comprise the phosphorylation levels of phosphorylation sites present in the peptide markers as listed in Table 1.

The term "peptide markers" in the context of the present invention refers to the fact that the peptides as listed in Table 1 can be preferably used according to the methods of the present invention to measure the phosphorylation levels of phosphorylation sites of said markers in samples. The phosphorylation levels of the individual phosphorylation sites present in said markers may be measured and compared in different ways. Therefore the present invention is not limited to the use of peptides identical to any of these peptide markers as listed in Table 1 as such. The skilled person may easily on the basis of the peptide markers listed in Table 1 design variant peptides compared to the specific peptides in said Table and use such variant peptides in a method for measuring phosphorylation levels of phosphorylation sites common to said peptide markers as listed in Table 1. These variant peptides may have one or more (2, 3, 4, 5, 6, 7, etc.) amino acids more or less than the given peptides and may also have amino acid substitutions (preferably conservative amino acid substitutions) as long as these variant peptides retain at least one or more of the phosphorylation sites of said original peptides as listed in said tables. Further the skilled person may also easily carry out the methods according to the present invention by using proteins (full length or N- or C-terminally truncated) comprising the amino acid regions of the "peptide markers" listed in Table 1 as sources for studying the phosphorylation of sites present in the amino acid regions of the peptides listed in Table 1. Also the skilled person may use peptide mimetics.

The protein kinase substrates as used in the methods described herein, are meant to include peptides, proteins or peptide mimetics comprising, preferably one or more, of the phosphorylation sites of the peptide markers of Table 1. Said one or more phosphorylation sites are specifically phosphorylated by the protein kinases present in the sample thereby providing a phosphorylation profile. More preferably the protein kinase substrates (peptides, proteins or peptide mimetics) as used in the method of the present invention comprise at least 5, at least 10, or at least 20, peptide markers as listed Table 1. More particularly said protein kinase substrates represent the one or more phosphorylation sites present in at least 5, 6, 7, 8, 9, 10, 11, 12, 13, 14, 15, 16, 17, 18, 19, 20, 21 or 22 of the peptide markers listed in Table 1. Preferably, said protein kinase substrates represent the one or more phosphorylation sites present in at least 5 or at least 8 or at least 12 of the peptide markers listed in Table 1. In a more preferred embodiment the protein kinase substrates comprise or consist of, preferably one or more, phosphorylation sites present in all of the peptide markers listed in Table 1.

The skilled person will understand that when the number of peptide markers as listed in Table 1 increases, so will increase the specificity, accuracy and sensitivity of the method according to the present invention. The highest method accuracy will be obtained when all protein kinase substrates comprising the phosphorylation sites of all peptide markers as listed in Table 1 are used. The inventors have found that especially the peptide markers with SEQ ID NO 1, 2, 3, 4, 5, 6, 7, 8, 9, 10, 11, 12, 13, 14, 15, 16, 17, 18, 19, 20, 21 and 22, preferably SEQ ID NO 1, 2, 3, 4, 5, 6, 7, 8, 9, 10, 11, 12, 13, 14, 15, 16, 17, 18 and 19, more preferably SEQ ID NO: 3, 4, 5, 10, 11, 13, 14, 15, 16, 17, 18 and 20 or SEQ ID NO: 1, 2, 3, 4, 5, 6, 7, 8, 9, 10, 11 and 12, even more preferably SEQ ID NO: 4, 5, 11, 13, 14, 15, 16 and 20 or SEQ ID NO: 1, 2, 3, 4, 5, 6, 7 and 8, even more preferably SEQ ID NO: 5, 11, 13, 16 and 20, even more preferably SEQ ID NO:4, 14, 15 and 16, even more preferably SEQ ID NO: 4, 14 and 15, as listed in Table 1 enable the prediction of pharmacotherapy response in NSCLC patients, in particular patients treated with Nivolumab.

In certain embodiments, especially peptide markers with SEQ ID NO 4, 5, 6, 7, 8, 9, 10, 11, 12, 13, 14, 15, 16, 17, 18, 19, 20, 21 or 22 as listed in Table 1 enable the prediction of pharmacotherapy response in NSCLC patients, in particular patients treated with Nivolumab.

In certain embodiments, especially peptide markers with SEQ ID NO 1, 2, 3, 4, 5, 6, 7, 8, 9, 10, 11, 12, 13, 14, 15, 16, 17, 18 and 19 as listed in Table 1 enable the prediction of pharmacotherapy response in NSCLC patients, in particular patients treated with Nivolumab.

In certain embodiments, especially peptide markers with SEQ ID NO: 3, 4, 5, 10, 13, 14, 15, 17, 18 and 19 as listed in Table 1 enable the prediction of pharmacotherapy response in NSCLC patients, in particular patients treated with Nivolumab.

In certain embodiments, especially peptide markers with SEQ ID NO: 1, 2, 3, 4, 5, 6, 7, 8, 9, 10, 11, 12, 13, 14, 15, 16, 17, 18, 20, 21 and 22 as listed in Table 1 enable the prediction of pharmacotherapy response in NSCLC patients, in particular patients treated with Nivolumab.

In certain embodiments, especially peptide markers with SEQ ID NO: 3, 4, 5, 10, 13, 14, 15, 17 and 18 as listed in Table 1 enable the prediction of pharmacotherapy response in NSCLC patients, in particular patients treated with Nivolumab.

The peptide markers as listed in Table 1 could serve as an accurate early indicator for therapeutic response in a mammalian subject to measure the effectiveness of candidate NSCLC inhibitory agents.

In particular embodiments, a phosphorylation profile comprising the phosphorylation levels of phosphorylation sites present in at least 5 peptide markers as listed in Table 1 indicates that said phosphorylation profile comprises the phosphorylation levels of phosphorylation sites present in the 5 peptide markers with SEQ ID NO: 5, 11, 13, 16 and 20, and optionally the phosphorylation levels of phosphorylation sites present in one or more peptide markers as listed in Table 1 which are different from the peptide markers with SEQ ID NO: 5, 11, 13, 16 and 20.

In particular embodiments, a phosphorylation profile comprising the phosphorylation levels of phosphorylation sites present in at least 8 peptide markers as listed in Table 1 indicates that said phosphorylation profile comprises the phosphorylation levels of phosphorylation sites present in the 8 peptide markers with SEQ ID NO: 4, 5, 11, 13, 14, 15, 16 and 20 or SEQ ID NO: 1, 2, 3, 4, 5, 6, 7 and 8, and optionally the phosphorylation levels of phosphorylation sites present in one or more peptide markers as listed in Table 1 which are different from the peptide markers with SEQ ID NO: 4, 5, 11, 13, 14, 15, 16 and 20 or SEQ ID NO: 1, 2, 3, 4, 5, 6, 7 and 8, respectively.

In particular embodiments, a phosphorylation profile comprising the phosphorylation levels of phosphorylation sites present in at least 12 peptide markers as listed in Table 1 indicates that said phosphorylation profile comprises the phosphorylation levels of phosphorylation sites present in the 12 peptide markers with SEQ ID NO: 3, 4, 5, 10, 11, 13, 14, 15, 16, 17, 18 and 20 or SEQ ID NO: 1, 2, 3, 4, 5, 6, 7, 8, 9, 10, 11 and 12, and optionally the phosphorylation levels of phosphorylation sites present in one or more peptide markers as listed in Table 1 which are different from the peptide markers with SEQ ID NO: 3, 4, 5, 10, 11, 13, 14, 15, 16, 17, 18 and 20 or SEQ ID NO: 1, 2, 3, 4, 5, 6, 7, 8, 9, 10, 11 and 12, respectively.

TABLE 1 list of 22 peptide markers comprising phosphorylation sites used for determining the kinase activity, their sequence and SEQ ID NO. The name of the peptide markers refers to the associated proteins and to the start and the end position of the amino acid sequence.

Figure 1:
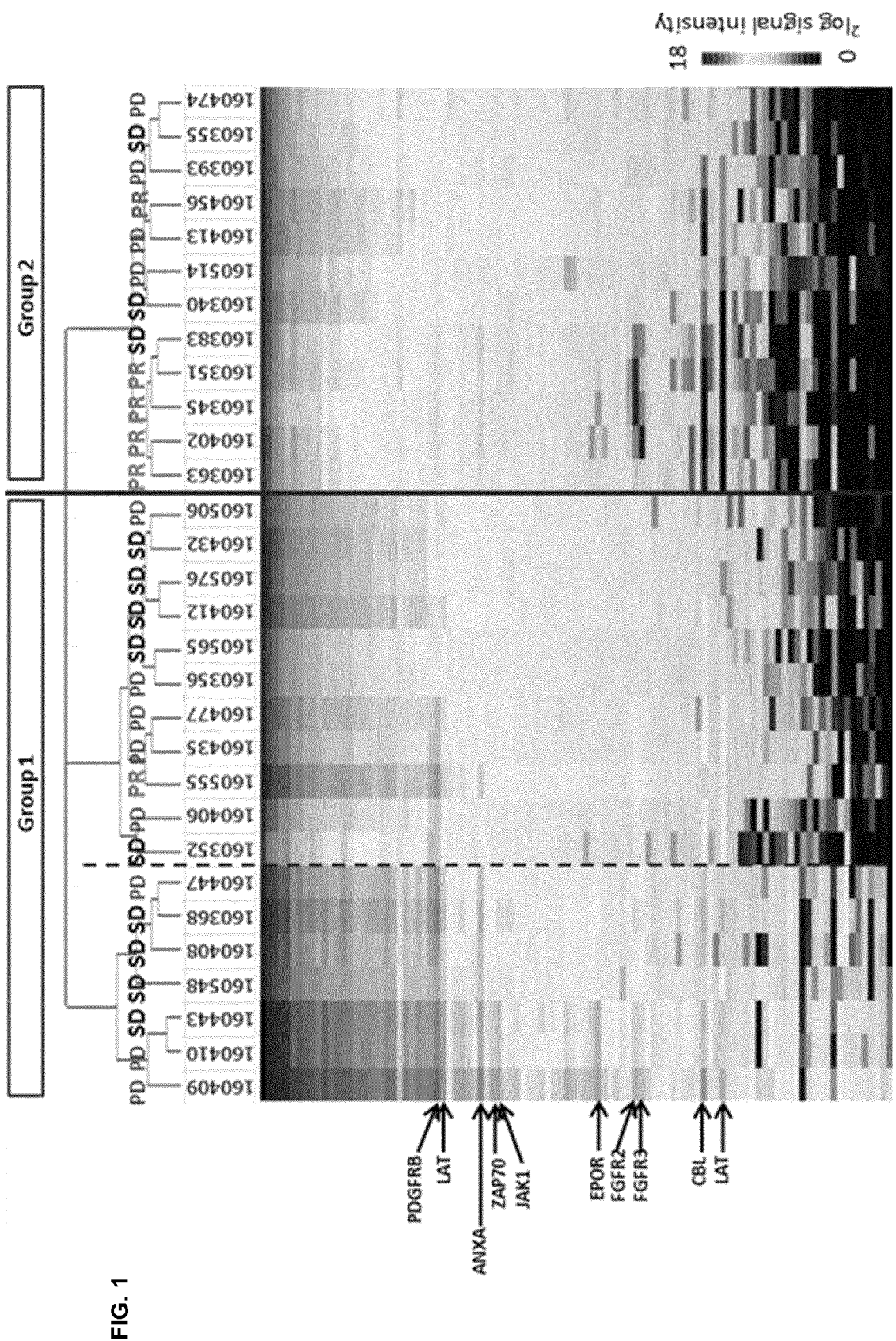
FIG. 1 shows an unsupervised (blinded) analysis of the protein tyrosine kinase (PTK) activity in 30 non-small cell lung cancer (NSCLC) patient-derived peripheral blood mononuclear cell (PBMC) samples and the kinase profiles correlation to patient response to Nivolumab. Hierarchical clustering analysis results in co-clustering of patients with partial response (PR). The differentiating signals in patients with PR are especially present on the LAT (SEQ ID NO: 4 and SEQ ID NO: 14) and CBL (SEQ ID NO: 15) phosphorylation sites. Abbreviations: PR, partial response; SD, stable disease; CBL, E3 ubiquitin-protein ligase CBL; EPOR, erythropoietin receptor; FGFR2/3, fibroblast growth factor receptor 2/3; JAK1, Tyrosine-protein kinase JAK1; LAT, linker for activation of T-cells family member 1; PDGFRB: platelet-derived growth factor receptor beta; ZAP70, tyrosine-protein kinase ZAP-70.
Figure 2:
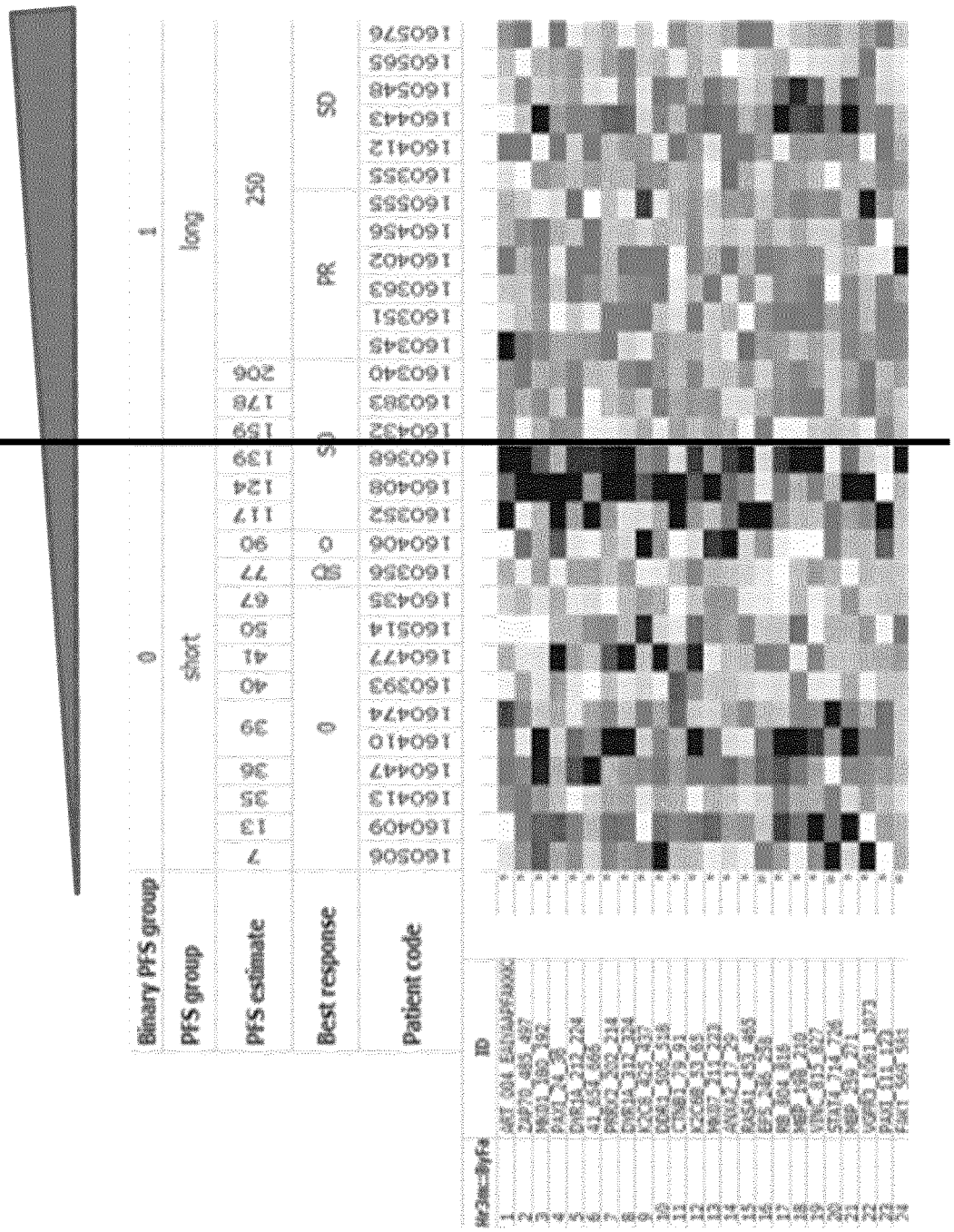
FIG. 2 shows the protein tyrosine kinase activity in 30 patient-derived peripheral blood mononuclear cell (PBMC) pre-treatment samples of non-small cell lung cancer (NSCLC) patients treated with Nivolumab, and the kinase profiles correlation with time to progression. The phosphorylation sites are sorted according to correlation with the progression-free survival (PFS) estimate, which is the time to progression with 'no progression' censored to 250 days. The differentiating signals in a long PFS estimate (>140 days) are especially present on the top-10 of peptide markers, consisting of artificial peptide no. 4 (ART_004; SEQ ID NO: 1), erb-b2 receptor tyrosine kinase 4 (ERBB4; SEQ ID NO: 2), fibroblast growth factor receptor 2 (FGFR2, SEQ ID NO: 3), linker for activation of T-cells (LAT, SEQ ID NO.
Figure 2:
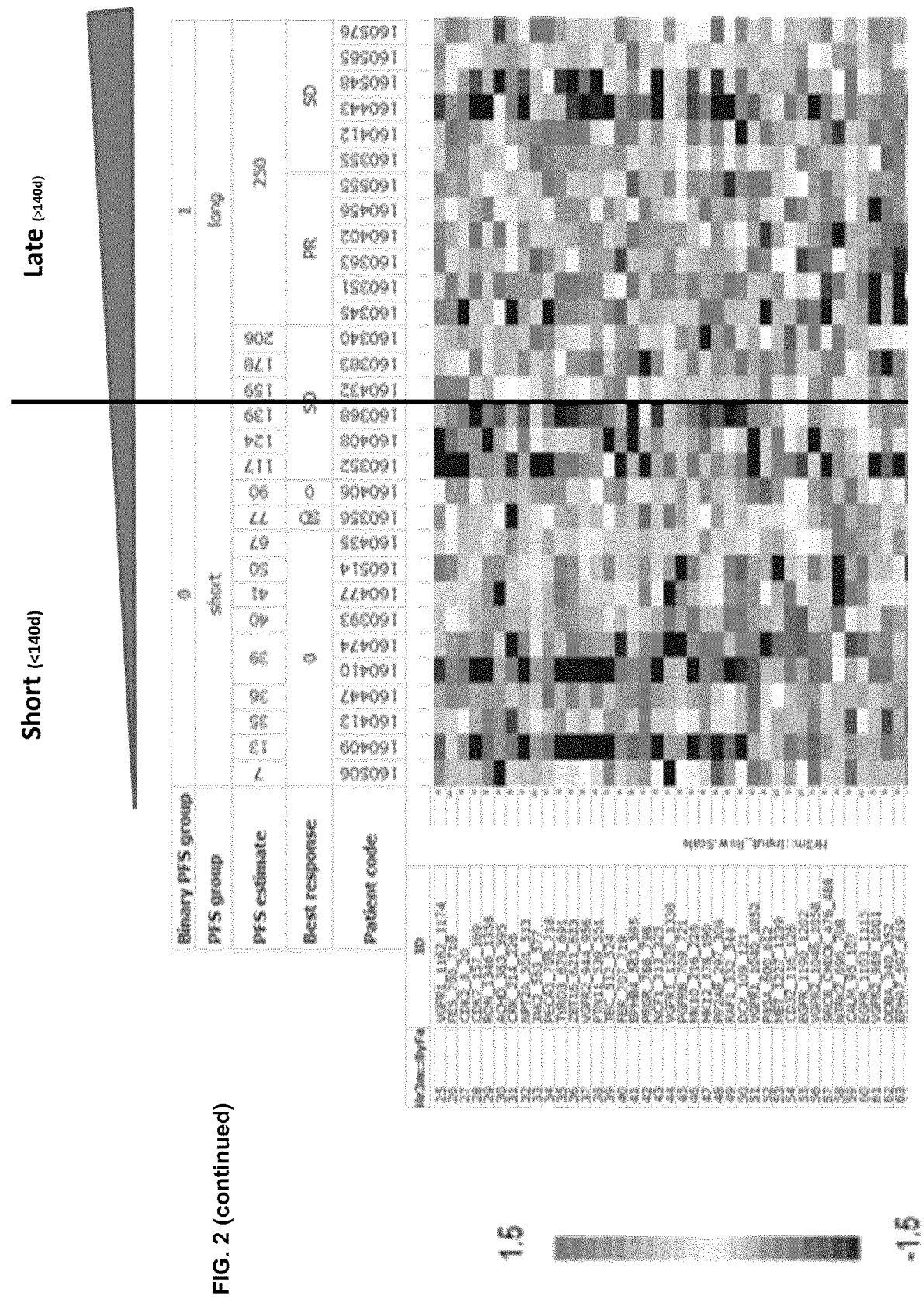
Figure 2:
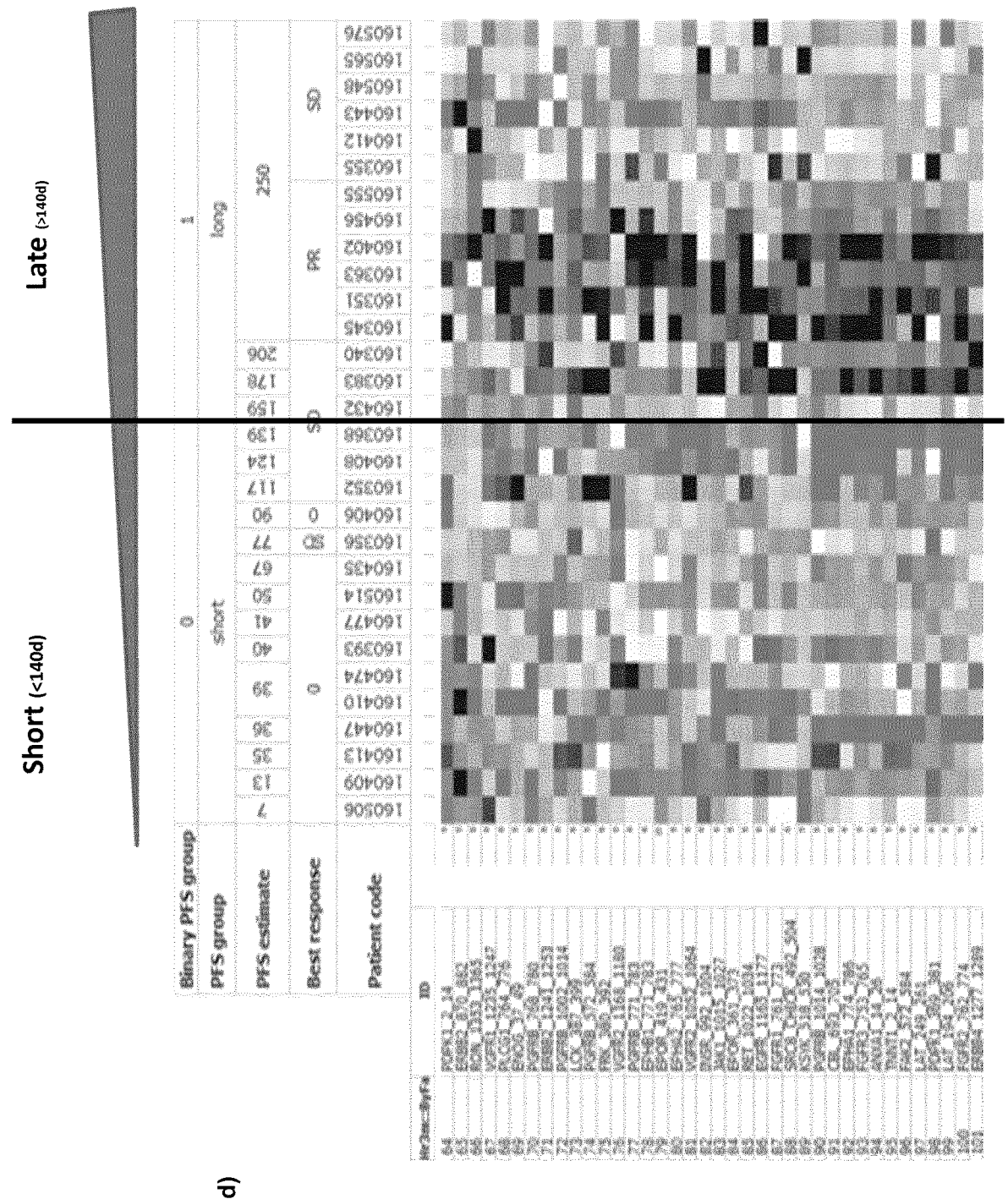

| SEQ ID NO | Name | Sequence | Reference |
|---|---|---|---|
| 1 | ART_004_EAIYAAP FAKKKXC | EAIYAAPFAKKK | FIG. 2 |
| 2 | ERBB4_1277_1289 | IVAENPEYLSEFS | FIG. 2 |
| 3 | FGFR2_762_774 | TLTTNEEYLDLSQ | FIG. 1, 2 |
| 4 | LAT_194_206 | MESIDDYVNVPES | FIG. 1, 2 |
| 5 | ZAP70_485_497 | ALGADDSYYTARS | FIG. 1, 2, 4 |
| 6 | MK01_180_192 | HTGFLTEYVATRW | FIG. 2 |
| 7 | FAK2_572_584 | RYIEDEDYYKASV | FIG. 2 |
| 8 | PAXI_24_36 | FLSEETPYSYPTG | FIG. 2 |
| 9 | TNNT1_2_14 | SDTEEQEYEEEQP | FIG. 2 |
| 10 | ANXA1_14_26 | IENEEQEYVQTVK | FIG. 1, 2 |
| 11 | DYR1A_212_224 | KHDTEMKYYIVHL | FIG. 2, 4 |
| 12 | 41_654_666 | LDGENIYIRHSNL | FIG. 2 |
| 13 | FGFR3_753_765 | TVTSTDEYLDLSA | FIG. 1, 2, 4 |
| 14 | LAT_249_261 | EEGAPDYENLQEL | FIG. 1, 2 |
| 15 | CBL_693_705 | EGEEDTEYMTPSS | FIG. 1, 2 |
| 16 | KSYK_518_530 | ALRADENYYKAQT | FIG. 2, 4 |
| 17 | PGFRB_1014_1028 | PNEGDNDYIIPLPDP | FIG. 1, 2 |
| 18 | EPOR_361_373 | SEHAQDTYLVLDK | FIG. 1, 2 |
| 19 | JAK1_1015_1027 | AIETDKEYYTVKD | FIG. 1 |
| 20 | PRRX2_202_214 | WTASSPYSTVPPY | FIG. 2, 4 |
| 21 | PDPK1_369_381 | DEDCYGNYDNLLS | FIG. 2 |
| 22 | EPHA1_774_786 | LDDFDGTYETQGG | FIG. 2 |

It should further be noted that according to a preferred embodiment of the present invention the peptide markers as listed in Table 1 can be used as such for carrying out the methods according to the present invention. The present invention however also includes the use of analogs and combinations of these peptide markers for use in the method according to the present invention. The peptide marker analogs include peptide markers which show a sequence identity of more than 70%, preferably more than 80% and more preferably more than 90%.

In yet another embodiment, the present invention relates to a method for predicting the response of a patient diagnosed with NSCLC cancer, to a medicament, comprising the steps of:

(a) measuring the kinase activity of a blood sample, obtained from said patient diagnosed with NSCLC, by contacting said sample with at least one protein kinase substrate, thereby providing a phosphorylation profile of said sample, said phosphorylation profile comprising the phosphorylation levels of phosphorylation sites present in at least 5, preferably at least 8 or at least 12, peptide markers as listed in Table 1; and, (c) calculating a classifier parameter from said phosphorylation profile; and (d) determining the response of said patient to said medicament on the basis of said classifier parameter.

By establishing a classifier parameter for determining the prediction of pharmacotherapy response of the NSCLC patient the method of the present invention provides a criterion for analysing the results obtained from the method of the present invention. This criterion enables a person to provide a prediction or prognosis on the basis of a single or limited number of data. The person providing the prediction or prognosis does not have to interpret an entire set of data, but rather bases his conclusion on the basis of a single or limited number of criteria.

The term "classifier parameter" as used herein is a discriminating value which has been determined by establishing the phosphorylation profile of a sample obtained from a patient suffering from NSCLC. Said discriminating value identifies the prediction of response to pharmacotherapy of NSCLC patients. The classifier parameter includes information regarding the phosphorylation level of several protein kinase substrates. Classification is a procedure in which individual items are placed into groups based on quantitative information on one or more characteristics inherent in the items (e.g. phosphorylation levels or profiles of a sample) and based on a training set of previously labelled items (clinical response to a pharmacotherapy). The classifier parameter is calculated by applying a "classifier" to the measured phosphorylation levels of a sample. Based on the classifying parameter a sample is assigned to (or predicted to belong to) a class (predicting the pharmacotherapy response of said patient). The classifier has been previously determined by comparing samples which are known to belong to the respective relevant classes. For instance the classifier may be a mathematical function that uses information regarding the phosphorylation level of several protein kinase substrates which individual protein kinase substrates can be statistically weighted based on the measured phosphorylation level of a number of protein kinase substrates (or values derived from that). Several methods are known in the art for developing a classifier including the neural network (Multi-layer Perceptron), support vector machines, k-nearest neighbours, Gaussian mixture model, naive bayes, decision tree, RBF classifiers, random forest, discriminant analysis, linear discriminant analysis, quadratic discriminant analysis, discriminant analysis-principal component analysis, partial least squares discriminant analysis, generalized distance regression and elastic net classification. The classifier parameter determined in this manner is valid for the same experimental setup in future individual tests.

It is not relevant to give an exact threshold value for the classifier parameter. A relevant threshold value can be obtained by correlating the sensitivity and specificity and the sensitivity/specificity for any threshold value. A threshold value resulting in a high sensitivity results in a lower specificity and vice versa. If one wants to increase the positive predictive value of the test to determine whether NSCLC patient will respond to targeted pharmacotherapy, then the threshold value of the test can be changed which as a consequence will decrease the negative predictive value of the test to determine whether NSCLC patient will not respond to targeted pharmacotherapy. If one wants to increase the negative predictive value of the test to determine whether NSCLC patient will not respond to targeted pharmacotherapy, then the threshold value can be changed in the opposite direction which as a consequence will decrease the positive predictive value of the test to determine whether NSCLC patient will respond to targeted pharmacotherapy It is thus up to the diagnostic engineers to determine which level of positive predictive value/negative predictive value/sensitivity/specificity is desirable and how much loss in positive or negative predictive value is tolerable. The chosen threshold level could be dependent on other diagnostic parameters used in combination with the present method by the diagnostic engineers.

In yet another embodiment, the present invention relates to a method according to the present invention wherein said classifier parameter predicts the response of said patient to said medicament if said classifier parameter is above a first predetermined threshold level, and wherein said classifier parameter indicates non-response to said medicament of said patient if said classifier parameter is below a second predetermined threshold level.

According to another embodiment, the present invention relates to the method of the present invention wherein said differential phosphorylation level or said classifier parameter indicates a response, no-response or undetermined or intermediate prediction of said medicament or the effect of the targeted pharmacotherapy of said patient.

As used in the present application the prediction of response to targeted pharmacotherapy of NSCLC patients is generally divided into two types of non-responders and responders and additionally some undetermined or intermediate responders. Whereas responders to a targeted pharmacotherapy will survive longer or have additional clinical benefits (e.g. improved quality of life, prolonged progression free survival, etc.) due to the treatment, the non-responders or the patients developing resistance to a targeted pharmacotherapy will not benefit from the targeted pharmacotherapy. The method of the present invention specifically enables the distinction between responders (e.g. complete response (CR), partial response (PR), stable disease (SD)) and non-responders (e.g. progressive disease (PD)) to a targeted pharmacotherapy or between patients with an early (e.g. <140 days after initiation of therapy) and late (e.g. >140 days after initiation of therapy) progression of disease upon treatment with a targeted pharmacotherapy.

The medicament as used in the method of the present invention can be any kind of chemical substance for instance used in the treatment, cure, prevention, or diagnosis of disease or used to otherwise enhance physical or mental well-being. Specifically said medicament can be an immunotherapeutic antibody, more preferably an immunotherapeutic antibody directed against an immune checkpoint, even more preferably an immunotherapeutic antibody directed against CTLA-4, PD-1 or PD-L1.

As used herein, the term "immunotherapeutic antibody" refers to a type of antibody, preferably a monoclonal antibody, which binds to a specific cell or protein, preferably a cell surface protein, and thereby stimulates the immune system to attack those cells. The immunotherapeutic antibody is used in the treatment, cure, prevention, or diagnosis of disease or used to otherwise enhance physical or mental well-being.

As used herein, the term "immune checkpoint" refers to an inhibitory pathways hardwired into the immune system that is crucial for maintaining self-tolerance and modulating the duration and amplitude of physiological immune responses in peripheral tissues in order to minimize collateral tissue damage. Tumors can designate one or multiple immune-checkpoint pathways as a major mechanism of immune resistance, particularly against T cells that are specific for tumor antigens. Immune checkpoints can be blocked by antibodies. Examples of such immune checkpoints are CTLA-4, PD-1 and PD-L1.

More preferably the present invention relates to a method according to the present invention wherein said medicament is Nivolumab, Pembrolizumab, Ipilimumab, Pidilizumab, Avelumab, Durvalumab, BMS-936559, Atezolizumab and/or a combination thereof and/or analogues thereof. Preferably said medicament is Nivolumab, Pembrolizumab, BMS-936559, Atezolizumab, Ipilimumab, Pidilizumab, Avelumab, or Durvalumab. Even more preferably, said medicament is Nivolumab.

Another a further embodiment, the kinase substrates carrying phosphorylation sites according to the present invention are located or immobilized on a solid support, and preferably a porous solid support. Preferably said immobilized kinase substrates carrying phosphorylation sites will be immobilized proteins, peptides or peptide mimetics. More preferably, the peptides are immobilized on a solid support.

As used herein "peptide" refers to a short truncated protein generally consisting of 2 to 100, preferably 2 to 30, more preferably 5 to 30 and even more preferably 13 to 18 naturally occurring or synthetic amino acids which can also be further modified including covalently linking the peptide bonds of the alpha carboxyl group of a first amino acid and the alpha amino group of a second amino acid by eliminating a molecule of water. The amino acids can be either those naturally occurring amino acids or chemically synthesized variants of such amino acids or modified forms of these amino acids which can be altered from their basic chemical structure by addition of other chemical groups which can be found to be covalently attached to them in naturally occurring compounds.

As used herein "protein" refers to a polypeptide made of amino acids arranged in a linear chain and joined together by peptide bonds between the carboxyl and amino groups of adjacent amino acid residues.

As used herein "peptide mimetics" refers to organic compounds which are structurally similar to peptides and similar to the peptide sequences list in Table 1. The peptide mimetics are typically designed from existing peptides to alter the molecules characteristics. Improved characteristics can involve, for example improved stability such as resistance to enzymatic degradation, or enhanced biological activity, improved affinity by restricted preferred conformations and ease of synthesis. Structural modifications in the peptidomimetic in comparison to a peptide, can involve backbone modifications as well as side chain modification.

For measuring the kinase activity of the sample a large variety of methods and formats are known in the art. The kinase activity can for example be measured using ELISA and multiplex ELISA techniques, blotting methods, mass spectrometry, surface plasmon resonance, capillary electrophoresis, bead arrays, macroarrays, microarrays or any other method known in the art. Depending on the type of kinase activity measurement method the solid support on which the proteins, peptides or peptide mimetics are fixed may vary.

Whereas in ELISA the protein kinase substrates are attached to the surface of the microtiterplates, in microarrays the protein kinase substrates are immobilized on and/or in the microarray substrate. Alternatively the substrates are synthesized in-situ direct on the microarray substrate.

In a preferred embodiment of the present invention the protein kinase a substrates are immobilized on an array, and preferably a microarray of protein kinase substrates wherein the protein kinase substrates are immobilized onto a solid support or another carrier. The immobilization can be either the attachment or adherence of two or more protein kinase substrate molecules to the surface of the carrier including attachment or adherence to the inner surface of said carrier in the case of e.g. a porous or flow-through solid support.

In a preferred embodiment of the present invention, the array of protein kinase substrates is a flow-through array. The flow-through array as used herein could be made of any carrier material having oriented through-going channels as are generally known in the art, such as for example described in PCT patent publication WO 01/19517. Typically the carrier is made from a metal oxide, glass, silicon oxide or cellulose. In a particular embodiment the carrier material is made of a metal oxide selected from the group consisting of zinc oxide, zirconium oxide, tin oxide, aluminium oxide, titanium oxide and thallium; in a more particular embodiment the metal oxide consists of aluminium oxide.

Accordingly, in a further embodiment of the present invention said array is a Pamchip®. In a further embodiment, the present invention relates to a method according to the present invention wherein said solid support (microarray) comprises at least 5, at least 10, at least 20, of the peptide markers as listed in Table 1 immobilized thereto.

In a further embodiment, the present invention relates to a method according to the present invention wherein said solid support (microarray) comprises at least 5, 6, 7, 8, 9, 10, 11, 12, 13, 14, 15, 16, 17, 18, 19, 20, 21 or 22 of the peptide markers as listed in Table 1 immobilized thereto. Preferably, the present invention relates to a method according to the present invention wherein said solid support (microarray) comprises at least 5 or at least 8 or at least 12 of the peptide markers as listed in Table 1 immobilized thereto.

In a further embodiment, the present invention relates to a method according to the present invention wherein said solid support (microarray) comprises each of the peptide as listed in Table 1 immobilized thereto.

In a further embodiment, the present invention relates to a method according to the present invention wherein said NSCLC is adenocarcinoma or squamous cell carcinoma.

In a further embodiment, the present invention relates to a method according to the present invention wherein said NSCLC is stage IV NSCLC.

In a further embodiment, the present invention relates to a method according to the present invention wherein said NSCLC is stage IV adenocarcinoma or squamous cell carcinoma.

Phosphorylation levels can also be measured according to the invention, without the necessity to generate phosphorylation profiles thereof. Also for this embodiment, the amount and the type of peptides, proteins or peptide mimetics to be used is as described above.

Another embodiment of the present invention regards the use of the method according to the present invention for assessing susceptibility to a medicament of a patient having non-small-cell lung carcinoma.

Another embodiment of the present invention regards the use of the method according to the present invention for assessing the pharmaceutical value of a medicament.

Another embodiment of the present invention regards the use of the method according to the present invention for assessing the clinical value of a medicament.

As used herein when assessing susceptibility to a drug, the pharmaceutical value of a drug or the clinical value of a drug, this comprises the assessment of the resistance of a subject or patient to said medicament. The present invention also relates in another embodiment to a computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out the method according to the present invention.

The present invention further relates to a computer system comprising a processor, and a memory coupled to said processor and encoding one or more programs, wherein said one or more programs instruct the processor to carry out the methods according to the present invention.

The present invention also relates in another embodiment to a kit for determining the response of a patient diagnosed with NSCLC, to a medicament, comprising at least one array comprising at least 5, preferably at least 10, more preferably at least 20, peptide markers as listed in Table 1, and a computer readable storage medium having recorded thereon one or more programs for carrying out the method according to the present invention. In a particular embodiment, the at least one array comprises at least 5, 6, 7, 8, 9, 10, 11, 12, 13, 14, 15, 16, 17, 18, 19, 20, 21 or 22 of the peptide markers as listed in Table 1. Preferably, the at least one array comprises at least 5 or at least 8 or at least 12 of the peptide markers as listed in Table 1.

The present invention further relates in yet another embodiment to the use at least 5, preferably at least 10, more preferably at least 20, peptide markers as listed in Table 1 for predicting the response of a patient diagnosed with NSCLC cancer to a medicament.

In a particular embodiment, the present invention relates to the use of at least 5, 6, 7, 8, 9, 10, 11, 12, 13, 14, 15, 16, 17, 18, 19, 20, 21 or 22 of the peptide markers as listed in Table 1 for predicting the response of a patient diagnosed with NSCLC cancer to a medicament. Preferably, the present invention relates to the use of at least 5 or at least 8 or at least 12 of the peptide markers as listed in Table 1 for predicting the response of a patient diagnosed with NSCLC cancer to a medicament. In a particular embodiment, the present invention relates to the use of the peptide markers as listed in Table 1 for predicting the response of a patient diagnosed with NSCLC to a medicament.

Since the present inventors have identified a surprisingly useful set of peptide markers to be used in methods for determining the prediction of response to a targeted pharmacotherapy of a patient suffering from NSCLC, the skilled man may carry out any method as defined above wherein he measures the kinase activity of any of the peptide markers of Table 1. Also this method may be carried out using the amount and type of peptides, proteins or protein mimetics as defined above. The formats for carrying out these methods are also as for the methods described above.

Furthermore, the inventors have also surprisingly found that the aberrant activity of TAM family receptor tyrosine kinases (RTKs), including MER proto-oncogene tyrosine kinase (MERTK), TYRO3 protein tyrosine kinase (TYRO3) and/or AXL receptor tyrosine kinase (AXL), can be used as "universal markers" for predicting the response of a patient diagnosed with cancer, to a medicament, and that the aberrant activity of the TAM family RTKs is preferably determined by establishing a phosphorylation profile comprising the phosphorylation levels of phosphorylation sites present in at least peptide markers ZAP70 (SEQ ID NO:5), PRRX2 (SEQ ID NO: 20) and KSYK (SEQ ID NO: 16) as listed in Table 1, more preferably in at least peptide markers ZAP70 (SEQ ID NO:5), DYR1A (SEQ ID NO: 11), FGFR3 (SEQ ID NO: 13), KSYK (SEQ ID NO: 16) and PRRX2 (SEQ ID NO: 20) as listed in Table 1.

Moreover, the inventors found by upstream kinase analysis that the TAM family of receptor tyrosine kinases (RTKs) is at least in part responsible for the phosphorylation profile comprising the phosphorylation levels of phosphorylation sites present in at least 5 peptide markers as listed in Table 1, especially in peptide markers ZAP70 (SEQ ID NO:5), DYR1A (SEQ ID NO: 11), FGFR3 (SEQ ID NO: 13), KSYK (SEQ ID NO: 16) and/or PRRX2 (SEQ ID NO: 20) as listed in Table 1, and therefore, the aberrant activity of the TAM family of receptor tyrosine kinases (RTKs) may especially be used for predicting the response of a patient diagnosed with NSCLC, to a medicament.

The term "TAM family of receptor tyrosine kinases" as used herein refers to a family of transmembrane proteins, namely receptor tyrosine kinases, which transduce signals from the extracellular environment to the cytoplasm and nucleus. The TAM family of RTKs is distinguished from other RTK families by a conserved amino acid sequence, KW (I/L)A(I/L)ES, within the kinase domain (cytosolic region). Also the adhesion molecule-like domains in the extracellular region have conserved sequences. Non-limiting examples of members of the TAM family of RTKs include MERTK, TYRO-3 and AXL, which is also known as UFO.

Exemplary human (*Homo sapiens*) members of the TAM family of RTKs include
- AXL receptor tyrosine kinase with NCBI Genbank Gene ID: 558, Swissprot entry P30530, Genbank RefSeq for one representative amino acid sequence followed by the Genbank sequence version NP_001265528.1 and Genbank RefSeq for one representative mRNA sequence followed by the Genbank sequence version NM_001278599.1;
- MER proto-oncogene, tyrosine kinase with NCBI Genbank Gene ID: 10461, Swissprot entry Q12866, Genbank RefSeq for one representative amino acid sequence followed by the Genbank sequence version NP_006334.2 and Genbank RefSeq for one representative mRNA sequence followed by the Genbank sequence version NM_006343.2; and
- TYRO3 protein tyrosine kinase with NCBI Genbank Gene ID: 7301, Swissprot entry: Q06418, Genbank RefSeq for one representative amino acid sequence followed by the Genbank sequence version NP_001317193.1 and Genbank RefSeq for one representative mRNA sequence followed by the Genbank sequence version NM_001330264.1.

In view of the above, another aspect provides a method for predicting the response of a patient diagnosed with cancer, to a medicament, comprising the steps of
(a) measuring the kinase activity of at least one member of the TAM family of RTKs in a sample, obtained from said patient diagnosed with cancer,
(b) determining from said kinase activity of at least one member of the TAM family of RTKs the response of said patient to said medicament.

In particular embodiments, said at least one member of the TAM family of RTKs is MERTK, TYRO3 and/or AXL. Preferably, said at least one member of the TAM family of RTKs is MERTK.

The kinase activity of said at least one member of the TAM family of RTKs may be determined by any means known in the art to determine kinase activity.

In particular embodiments, the kinase activity of said at least one member of the TAM family of RTKs may be determined by contacting the sample with at least one protein kinase substrate, thereby providing a phosphorylation profile of said sample, said phosphorylation profile comprising the phosphorylation levels of phosphorylation sites present in at least ZAP70 (SEQ ID NO:5), PRRX2 (SEQ ID NO: 20) and/or KSYK (SEQ ID NO: 16) as listed in Table 1, preferably in at least ZAP70 (SEQ ID NO: 5), DYR1A (SEQ ID NO: 11), FGFR3 (SEQ ID NO: 13), KSYK (SEQ ID NO: 16) and/or PRRX2 (SEQ ID NO: 20) as listed in Table 1, more preferably all peptide markers as listed in Table 1.

In particular embodiments, the kinase activity of said at least one member of the TAM family of RTKs may be determined by contacting the sample with at least one protein kinase substrate, thereby providing a phosphorylation profile of said sample, said phosphorylation profile comprising the phosphorylation levels of phosphorylation sites present in at least 3, 4 or 5 of the peptide markers ZAP70 (SEQ ID NO: 5), DYR1A (SEQ ID NO: 11), FGFR3 (SEQ ID NO: 13), KSYK (SEQ ID NO: 16) and PRRX2 (SEQ ID NO: 20) as listed in Table 1, preferably in at least ZAP70 (SEQ ID NO:5), PRRX2 (SEQ ID NO: 20) and KSYK (SEQ ID NO: 16) as listed in Table 1, more preferably in at least ZAP70 (SEQ ID NO:5), PRRX2 (SEQ ID NO: 20) and KSYK (SEQ ID NO: 16), and DYR1A (SEQ ID NO: 11) or FGFR3 (SEQ ID NO: 13), as listed in Table 1, even more preferably in all five of ZAP70 (SEQ ID NO: 5), DYR1A (SEQ ID NO: 11), FGFR3 (SEQ ID NO: 13), KSYK (SEQ ID NO: 16) and PRRX2 (SEQ ID NO: 20) as listed in Table 1.

In particular embodiments, said sample is obtained from a patient diagnosed with cancer.

In particular embodiments, said sample is derived from peripheral blood, or immune cells isolated or enriched from peripheral blood (e.g. peripheral blood mononuclear cells, PBMCs).

In particular embodiments, said sample is derived from tumor tissues, preferably tumor tissues containing infiltrated immune cells like tumor-infiltrated T-cells (TILs) or macrophages.

The term "cancer" as used herein, refers to malignant neoplasm characterized by deregulated or unregulated cell growth. In certain embodiments, the cancer may be selected from the group consisting of squamous cell cancer (e.g., epithelial squamous cell cancer), lung cancer including small-cell lung cancer, non-small cell lung cancer, adenocarcinoma of the lung, squamous carcinoma of the lung and large cell carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, head cancer and neck cancer.

The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

In particular embodiments, said cancer may be selected from the group consisting of lung cancer, skin cancer (e.g. melanoma), renal cancer, bladder cancer, head and neck cancers, ovarian cancer, uterine cancer, gastroesophageal cancers and blood cancer.

In particular embodiments, said cancer may be selected from the group consisting of highly mutated cancers of lung cancer, skin cancer (e.g. irresectable stage IIIc or IV melanoma), renal cancer, bladder cancer, head and neck cancers, ovarian cancer, uterine cancer, gastroesophageal cancers and blood cancer.

In particular embodiments, said cancer may be selected from the group consisting of a metastatic form of lung cancer (e.g. stage IV NSCLC), skin cancer (e.g. irresectable stage IIIc or IV melanoma), renal cancer, bladder cancer, head and neck cancers, ovarian cancer, uterine cancer, gastroesophageal cancers and blood cancer. In particular embodiments, said cancer is NSCLC.

In particular embodiments, said cancer is head and/or neck cancer, preferably a head or neck cancer selected from the group consisting of oral cavity cancer, pharynx cancer, larynx cancer, salivary gland cancer, paranasal sinuses cancer and nasal cavity cancer, more preferably an advanced form of a head or neck cancer selected from the group consisting of oral cavity cancer, pharynx cancer, larynx cancer, salivary gland cancer, paranasal sinuses cancer and nasal cavity cancer.

In particular embodiments, said cancer is stage IV NSCLC.

In particular embodiments, said medicament is an immunotherapeutic antibody, more preferably an immunotherapeutic antibody directed against an immune checkpoint, even more preferably an immunotherapeutic antibody directed against CTLA-4, PD-1 or PD-L1. Non-limiting examples of immunotherapeutic antibody directed against PD-1 or PD-L1 include Nivolumab, Prembrolizumab, BMS-936559, Atezolizumab, Ipilimumab, Pidilizumab, Avelumab, Durvalumab and/or analogues thereof.

In particular embodiments, said medicament is chosen from the group consisting of Nivolumab, Prembrolizumab, BMS-936559, Atezolizumab, Ipilimumab, Pidilizumab, Avelumab and Durvalumab.

The present invention also provides a kit for determining the response of a patient diagnosed with cancer to a medicament, comprising at least one array comprising at least ZAP70 (SEQ ID NO:5), PRRX2 (SEQ ID NO: 20) and KSYK (SEQ ID NO: 16) as listed in Table 1, preferably at least ZAP70 (SEQ ID NO: 5), DYR1A (SEQ ID NO: 11), FGFR3 (SEQ ID NO: 13), KSYK (SEQ ID NO: 16) and PRRX2 (SEQ ID NO: 20) as listed in Table 1, more preferably all peptide markers as listed in Table 1, and a computer readable storage medium having recorded thereon one or more programs for carrying out the method as taught herein.

Another aspect provides a computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out the method comprising measuring the kinase activity of at least one member of the TAM family of RTKs in a sample, obtained from said patient diagnosed with cancer, as taught herein.

Another embodiment of the present invention regards the use of the method comprising measuring the kinase activity of at least one member of the TAM family of RTKs, preferably the kinase activity of MERTK, in a sample, obtained from said patient diagnosed with cancer, as taught herein, for assessing susceptibility to a medicament of a patient having cancer.

Another embodiment of the present invention regards the use of the method comprising measuring the kinase activity of at least one member of the TAM family of RTKs, preferably the kinase activity of MERTK, in a sample, obtained from said patient diagnosed with cancer, as taught herein, for assessing the pharmaceutical value of a medicament.

Another embodiment of the present invention regards the use of the method comprising measuring the kinase activity of at least one member of the TAM family of RTKs, preferably the kinase activity of MERTK, in a sample, obtained from said patient diagnosed with cancer, as taught herein, for assessing the clinical value of a medicament.

The present invention further relates in yet another embodiment to the use the activity of the TAM family of RTKs, preferably the activity of MERTK, TYRO3 and/or AXL, more preferably the activity of MERTK, for predicting the response of a patient diagnosed with cancer to a medicament.

The skilled person will understand that all particular embodiments relating to the method for predicting the response of a patient diagnosed with non-small-cell lung carcinoma, to a medicament, comprising the steps of: (a) measuring the kinase activity of a blood sample, obtained from said patient diagnosed with non-small-cell lung carcinoma, by contacting said sample with at least one protein kinase substrate, thereby providing a phosphorylation profile of said sample, said phosphorylation profile comprising the phosphorylation levels of phosphorylation sites present in at least 5, preferably at least 8 or at least 12, peptide markers as listed in Table 1; and, (b) determining from said phosphorylation profile the response of said patient to said medicament, as taught herein, for example the particular embodiments relating to the calculation of a classifier parameter from said phosphorylation profile, the kit for determining the response of a patient and a computer program product, also apply to the method for predicting the response of a patient diagnosed with cancer, to a medicament, comprising the steps of (a) measuring the kinase activity of at least one member of the TAM family of RTKs in a sample, obtained from said patient diagnosed with cancer, (b) determining from said kinase activity of at least one member of the TAM family of RTKs the response of said patient to said medicament as taught herein.

The present invention is hereafter exemplified by the illustration of particular, non-limiting examples.

EXAMPLES

Example 1—NSCLC Patients with Short Term Progression and Late (or No) Progression at 3 Months to Nivolumab can be Differentiated According to Kinase Inhibition Profiles PBMCs were isolated from 30 NSCLC patients which were refractory to platinum-based therapy, of which 18 patients showed progression within 3 months (6 partial response (PR), 13 stable disease (SD) and 11 progressive disease (PD). Samples were taken 1-3 days before treatment onset. PBMCs were lysed in MPER buffer in the presence of protease and phosphatase inhibitors and 2 µg total protein was profiled for kinase activity using dynamic peptide microarrays (PamChip). The microarrays comprised 144 different peptides, being substrates from protein tyrosine kinases. Kinase activity was detected in real time kinetics using a fluorescently labelled anti-phosphotyrosine antibody. These profiles were analyzed in Matlab including a normalization step (variance stabilizing normalization, VSN) and 2-group comparison test, to identify differential signals in patients with early vs. late progression on Nivolumab.

In a first unsupervised hierarchical clustering analysis (of the blinded samples), samples of patients with a partial response (PR) to nivolumab co-clustered with differentiating signals primarily on the LAT (SEQ ID NO:4 and SEQ ID NO: 14) and CBL (SEQ ID NO:15) phosphorylation sites, but also on the PDGFRB (SEQ ID NO: 17), ANXA (SEQ ID NO: 10), ZAP70 (SEQ ID NO: 5), JAK1 (SEQ ID NO: 19), EPOR (SEQ ID NO: 18), FGFR2 (SEQ ID NO: 3), and FGFR3 (SEQ ID NO:13) phosphorylation sites (FIG. 1). In a subsequent supervised analysis, kinase activity profiles correlated with progression-free survival (PFS) (FIG. 2). Two different profiles were observed in patients with progression before or after day 140 significant in a two group comparison) (FIG. 2). The differentiating signals in a long PFS estimate (>140 days) are especially present on artificial peptide no. 4 (ART_004; SEQ ID NO: 1), erb-b2 receptor tyrosine kinase 4 (ERBB4; SEQ ID NO: 2), fibroblast growth factor receptor 2 (FGFR2, SEQ ID NO: 3), linker for activation of T-cells (LAT, SEQ ID NO: 4 and 14), zeta chain of T-cell receptor associated protein kinase 70 (ZAP70; SEQ ID NO: 5), mitogen-activated protein kinase 1 (MK01; SEQ ID NO 6), protein tyrosine kinase 2 beta (FAK2; SEQ ID NO: 7), Paxillin (PAXI; SEQ ID NO: 8) and 3-phosphoinositide-dependent protein kinase 1 (PDPK1; SEQ ID NO: 21) phosphorylation sites. Interestingly, the kinase activity profile provided a good prediction of the treatment outcome of patients treated with Nivolumab. Using the method according to the present invention it was possible to divide patients which are either early progressive (<140 days) or late (>140 days) or non-progressive to a treatment with Nivolumab (FIG. 3). Phosphorylation sites with SEQ ID NO: 1, 2, 3, 4, 5, 6, 7, 8, 9, 10, 11, 12, 13, 14, 15, 16, 17, 18, 20, 21 and 22, preferably SEQ ID NO: 4, 5, 11, 13, 14, 15, 16 and 20, more preferably SEQ ID NO: 5, 11, 13, 16 and 20, as listed in Table 1 were identified as key biomarkers for the differentiation between progressive and non/late-progressive patients.

Statistical analysis (2-group comparison) was performed differentiating early from late progressive patient profiles. The most significantly different peptide sequences, especially ZAP70 (SEQ ID NO: 5), DYR1A (SEQ ID NO: 11), FGFR3 (SEQ ID NO: 13), KSYK (SEQ ID NO: 16) and PRRX2 (SEQ ID NO: 20) as listed in Table 1, were analysed for putative upstream kinase activities which can induce their phosphorylation.

Information from the knowledge databases (HRPD, PhosphoSite, Reactome and PhosphoNET) was used and indicated higher activity of the TAM family of kinases, namely AXL, MERTK and TYRO3, in the late progressive patients (FIG. 4).

Example 2: Head and Neck Cancer Patients Responding or not Responding to PD-1 Blockers can be Differentiated According to Kinase Activity Profiles A clinical study is conducted using blood samples from patients with an advanced form of head and neck cancer, which were treated with PD-1 blockers. This allows a comparison with the clinical responses.

Statistical analysis (2-group comparison) is performed differentiating responding versus non-responding patient profiles. The most significantly different peptide sequences are analysed for putative upstream kinase activities which can induce their phosphorylation.

Information from the knowledge databases (HRPD, PhosphoSite, Reactome and PhosphoNET) is used to obtain markers for predicting the response of a patient diagnosed with an advanced form of head and neck cancer, to a PD1 blocker.

Example 3: Validation of TAM Family of RTKs as Universal Markers for Predicting the Response of a Patient Diagnosed with Cancer, to a Medicament A combined statistical analysis of the kinase activity profiles of Examples 1 and 2 is performed.

Information from the knowledge databases (HRPD, PhosphoSite, Reactome and PhosphoNET) is used to obtain markers for predicting the response of a patient diagnosed with cancer, to a medicament, preferably to a PD-1 blocker.

The invention claimed is:

1. A method for treating a patient diagnosed with non-small-cell carcinoma with a medicament selected from the group consisting of nivolumab, pembrolizumab, BMS-936559, atezolizumab, ipilimumab, pidilizumab, avelumab, and durvalumab, the method comprising:
   (1) obtaining a prediction of the response of the patient diagnosed with non-small-cell lung carcinoma to a medicament, wherein the prediction was obtained by a method comprising the steps of:
      (a) measuring the kinase activity of a blood sample, obtained from said patient diagnosed with non-small-cell lung carcinoma, by contacting said sample with at least one protein kinase substrate, thereby providing a phosphorylation profile of said sample, said phosphorylation profile comprising the phosphorylation levels of phosphorylation sites present in at least peptide markers with SEQ ID NO: 1, 2, 3, 4, 5, 6, 7, 8, 14 and 21; and
      (b) determining from said phosphorylation profile the response of said patient to said medicament; wherein the response of said patient to said medicament is determined from said phosphorylation profile by:
      (i) calculating a classifier parameter from said phosphorylation profile; and
      (ii) determining the response of said patient to said medicament on the basis of said classifier parameter; or
      wherein the response of said patient to said medicament is determined from said phosphorylation profile by
      (iii) comparing said phosphorylation profile to a first and a second reference phosphorylation profile; said first reference phosphorylation profile being representative for a good responder to said medicament and said second reference phosphorylation profile being representative for a poor responder to said medicament; and
      (iv) determining the response of said patient to said medicament on the basis of the comparison of said phosphorylation profile with said first and said second reference phosphorylation profile;
   wherein said medicament is selected from the group consisting of nivolumab, pembrolizumab, BMS-936559, atezolizumab, ipilimumab, pidilizumab, avelumab, and durvalumab; and
   (2) treating said patient with the medicament providing the best response in step (iv).

2. The method according to claim 1, wherein said blood sample comprises peripheral blood mononuclear cells.

3. The method according to claim 1, wherein said phosphorylation profiles comprise the phosphorylation levels of phosphorylation sites present in the peptide markers in SEQ ID Nos: 1-22.

4. The method according to claim 1, wherein said phosphorylation profile or said classifier parameter indicates good response, poor response or undetermined response of said patient to said medicament.

5. The method according to claim 1, wherein said non-small-cell lung carcinoma is a stage IV non-small-cell lung carcinoma.

6. The method according to claim 1, wherein from the measurements in step (a) the toxicity of said medicament in said patient is determined.

7. The method according to claim 1, for accessing susceptibility to medicament of a patient having non-small-cell lung carcinoma.

8. The method according to claim 1, for accessing pharmaceutical or clinical value of a medicament.

* * * * *

SEQUENCE LISTING

<160> NUMBER OF SEQ ID NOS: 22

<210> SEQ ID NO 1
<211> LENGTH: 12
<212> TYPE: PRT
<213> ORGANISM: artificial sequence
<220> FEATURE:
<223> OTHER INFORMATION: ART_004_EAIYAAPFAKKKXC

<400> SEQUENCE: 1

Glu Ala Ile Tyr Ala Ala Pro Phe Ala Lys Lys Lys

```
1               5                   10
```

<210> SEQ ID NO 2
<211> LENGTH: 13
<212> TYPE: PRT
<213> ORGANISM: artificial sequence
<220> FEATURE:
<223> OTHER INFORMATION: ERBB4_1277_1289

<400> SEQUENCE: 2

```
Ile Val Ala Glu Asn Pro Glu Tyr Leu Ser Glu Phe Ser
1               5                   10
```

<210> SEQ ID NO 3
<211> LENGTH: 13
<212> TYPE: PRT
<213> ORGANISM: artificial sequence
<220> FEATURE:
<223> OTHER INFORMATION: FGFR2_762_774

<400> SEQUENCE: 3

```
Thr Leu Thr Thr Asn Glu Glu Tyr Leu Asp Leu Ser Gln
1               5                   10
```

<210> SEQ ID NO 4
<211> LENGTH: 13
<212> TYPE: PRT
<213> ORGANISM: artificial sequence
<220> FEATURE:
<223> OTHER INFORMATION: LAT_194_206

<400> SEQUENCE: 4

```
Met Glu Ser Ile Asp Asp Tyr Val Asn Val Pro Glu Ser
1               5                   10
```

<210> SEQ ID NO 5
<211> LENGTH: 13
<212> TYPE: PRT
<213> ORGANISM: artificial sequence
<220> FEATURE:
<223> OTHER INFORMATION: ZAP70_485_497

<400> SEQUENCE: 5

```
Ala Leu Gly Ala Asp Asp Ser Tyr Tyr Thr Ala Arg Ser
1               5                   10
```

<210> SEQ ID NO 6
<211> LENGTH: 13
<212> TYPE: PRT
<213> ORGANISM: artificial sequence
<220> FEATURE:
<223> OTHER INFORMATION: MK01_180_192

<400> SEQUENCE: 6

```
His Thr Gly Phe Leu Thr Glu Tyr Val Ala Thr Arg Trp
1               5                   10
```

<210> SEQ ID NO 7
<211> LENGTH: 13
<212> TYPE: PRT
<213> ORGANISM: artificial sequence
<220> FEATURE:
<223> OTHER INFORMATION: FAK2_572_584

<400> SEQUENCE: 7

```
Arg Tyr Ile Glu Asp Glu Asp Tyr Tyr Lys Ala Ser Val
1               5                   10
```

```
<210> SEQ ID NO 8
<211> LENGTH: 13
<212> TYPE: PRT
<213> ORGANISM: artificial sequence
<220> FEATURE:
<223> OTHER INFORMATION: PAXI_24_36

<400> SEQUENCE: 8

Phe Leu Ser Glu Glu Thr Pro Tyr Ser Tyr Pro Thr Gly
1               5                   10

<210> SEQ ID NO 9
<211> LENGTH: 13
<212> TYPE: PRT
<213> ORGANISM: artificial sequence
<220> FEATURE:
<223> OTHER INFORMATION: TNNT1_2_14

<400> SEQUENCE: 9

Ser Asp Thr Glu Glu Gln Glu Tyr Glu Glu Glu Gln Pro
1               5                   10

<210> SEQ ID NO 10
<211> LENGTH: 13
<212> TYPE: PRT
<213> ORGANISM: artificial sequence
<220> FEATURE:
<223> OTHER INFORMATION: ANXA1_14_26

<400> SEQUENCE: 10

Ile Glu Asn Glu Glu Gln Glu Tyr Val Gln Thr Val Lys
1               5                   10

<210> SEQ ID NO 11
<211> LENGTH: 13
<212> TYPE: PRT
<213> ORGANISM: artificial sequence
<220> FEATURE:
<223> OTHER INFORMATION: DYR1A_212_224

<400> SEQUENCE: 11

Lys His Asp Thr Glu Met Lys Tyr Tyr Ile Val His Leu
1               5                   10

<210> SEQ ID NO 12
<211> LENGTH: 13
<212> TYPE: PRT
<213> ORGANISM: artificial sequence
<220> FEATURE:
<223> OTHER INFORMATION: 4100A0_654_666

<400> SEQUENCE: 12

Leu Asp Gly Glu Asn Ile Tyr Ile Arg His Ser Asn Leu
1               5                   10

<210> SEQ ID NO 13
<211> LENGTH: 13
<212> TYPE: PRT
<213> ORGANISM: artificial sequence
<220> FEATURE:
<223> OTHER INFORMATION: FGFR3_753_765

<400> SEQUENCE: 13

Thr Val Thr Ser Thr Asp Glu Tyr Leu Asp Leu Ser Ala
1               5                   10
```

-continued

```
<210> SEQ ID NO 14
<211> LENGTH: 13
<212> TYPE: PRT
<213> ORGANISM: artificial sequence
<220> FEATURE:
<223> OTHER INFORMATION: LAT_249_261

<400> SEQUENCE: 14

Glu Glu Gly Ala Pro Asp Tyr Glu Asn Leu Gln Glu Leu
1               5                   10

<210> SEQ ID NO 15
<211> LENGTH: 13
<212> TYPE: PRT
<213> ORGANISM: artificial sequence
<220> FEATURE:
<223> OTHER INFORMATION: CBL_693_705

<400> SEQUENCE: 15

Glu Gly Glu Glu Asp Thr Glu Tyr Met Thr Pro Ser Ser
1               5                   10

<210> SEQ ID NO 16
<211> LENGTH: 13
<212> TYPE: PRT
<213> ORGANISM: artificial sequence
<220> FEATURE:
<223> OTHER INFORMATION: KSYK_518_53000A0

<400> SEQUENCE: 16

Ala Leu Arg Ala Asp Glu Asn Tyr Tyr Lys Ala Gln Thr
1               5                   10

<210> SEQ ID NO 17
<211> LENGTH: 15
<212> TYPE: PRT
<213> ORGANISM: artificial sequence
<220> FEATURE:
<223> OTHER INFORMATION: PGFRB_1014_1028

<400> SEQUENCE: 17

Pro Asn Glu Gly Asp Asn Asp Tyr Ile Ile Pro Leu Pro Asp Pro
1               5                   10                  15

<210> SEQ ID NO 18
<211> LENGTH: 13
<212> TYPE: PRT
<213> ORGANISM: artificial sequence
<220> FEATURE:
<223> OTHER INFORMATION: EPOR_361_373

<400> SEQUENCE: 18

Ser Glu His Ala Gln Asp Thr Tyr Leu Val Leu Asp Lys
1               5                   10

<210> SEQ ID NO 19
<211> LENGTH: 13
<212> TYPE: PRT
<213> ORGANISM: artificial sequence
<220> FEATURE:
<223> OTHER INFORMATION: JAK1_1015_1027

<400> SEQUENCE: 19

Ala Ile Glu Thr Asp Lys Glu Tyr Tyr Thr Val Lys Asp
1               5                   10
```

```
<210> SEQ ID NO 20
<211> LENGTH: 13
<212> TYPE: PRT
<213> ORGANISM: artificial sequence
<220> FEATURE:
<223> OTHER INFORMATION: PRRX2_202_214

<400> SEQUENCE: 20

Trp Thr Ala Ser Ser Pro Tyr Ser Thr Val Pro Pro Tyr
1               5                   10

<210> SEQ ID NO 21
<211> LENGTH: 13
<212> TYPE: PRT
<213> ORGANISM: artificial sequence
<220> FEATURE:
<223> OTHER INFORMATION: PDPK1_369_381

<400> SEQUENCE: 21

Asp Glu Asp Cys Tyr Gly Asn Tyr Asp Asn Leu Leu Ser
1               5                   10

<210> SEQ ID NO 22
<211> LENGTH: 13
<212> TYPE: PRT
<213> ORGANISM: artificial sequence
<220> FEATURE:
<223> OTHER INFORMATION: EPHA1_774_786

<400> SEQUENCE: 22

Leu Asp Asp Phe Asp Gly Thr Tyr Glu Thr Gln Gly Gly
1               5                   10
```